(12) United States Patent
Ke et al.

(10) Patent No.: US 6,617,169 B2
(45) Date of Patent: Sep. 9, 2003

(54) TWO-DIMENSIONAL MR SPECTROSCOPY TECHNIQUES

(75) Inventors: Yong Ke, Belmont, MA (US); Perry F. Renshaw, Arlington, MA (US); Bruce Cohen, Lexington, MA (US)

(73) Assignee: McLean Hospital Corporation, Belmont, MA (US)

( * ) Notice: Subject to any disclaimer, the term of this patent is extended or adjusted under 35 U.S.C. 154(b) by 0 days.

(21) Appl. No.: 09/823,613

(22) Filed: Mar. 30, 2001

(65) Prior Publication Data

US 2002/0142367 A1 Oct. 3, 2002

(51) Int. Cl.[7] ............................................. G01N 24/00
(52) U.S. Cl. ........................ 436/173; 324/307; 324/308; 324/309; 324/310; 600/410
(58) Field of Search ................. 436/173; 324/307–310; 600/410, 416

(56) References Cited

U.S. PATENT DOCUMENTS 5,617,861 A * 4/1997 Ross et al. .................. 600/410
6,104,191 A * 8/2000 Hurd .......................... 324/310

OTHER PUBLICATIONS

Den Hollander et al. "Observation of GABA at 1.5 Tesla in the human brain using J–resolved licalized 1H–NMR spectroscopy", ISMRM Abstract, 1997, p. 1353.*

Keltner et al. "In vivo detection of GABA in human brain usng a localized double–quantum fiiletr technique", Magn. Reson. Medicine, 1997, v 37,(3), pp. 366–371.*

"Localized $^1$H NMR measurements of γ–aminobutyric acid in human brain in vivo" by D.L. Rothman et al., Neurobiology, vol. 90, pp. 5662–5666, Jun. 1993.

"Localized 2D J–Resolved [1]H MR Spectroscopy: Strong Coupling Effects In Vitro and In Vivo" by L. N. Ryner et al., Magnetic Resonance Imaging, vol. 13, No. 6, pp. 853–869, 1995.

"Detection of hidden metabolites by localized proton magnetic resonance spectroscopy in vivo" by O. M. Weber et al., Technology and Health Care, vol. 5, pp. 471–491, 1997.

"Proton MR spectroscopy of prostatic tissue focused on the detection of spermine, a possible biomarker of malignant behavior in prostate cancer" by M. van der Graaf et al., Magnetic Resonance Materials in Physics, Biology and Medicine, vol. 10, pp. 153–159, 2000.

"The Future of Magnetic Resonance Spectroscopy and Spectroscopic Imaging" by A.A. Maudsley and M.W. Weiner, http://www.sf.med.va.gov/mrs/PAPERS/Futrmrs.htm (8 pp.).

"Proton Magnetic Resonance Spectroscopy: An Emerging Technology in Pediatric Neurology Research" by E. Novotny et al., http://www.wwilkins.com/PDR/0031–39987–98p1.html (17 pp.).

* cited by examiner

*Primary Examiner*—Jill Warden
*Assistant Examiner*—Yelena Gakh
(74) *Attorney, Agent, or Firm*—Fish & Richardson P.C.

(57) ABSTRACT

The invention features methods of selecting chemical peaks from two-dimensional magnetic resonance spectra for one-dimensional extraction and quantification methods using these one-dimensional extractions. The methods permit enhanced differentiation of particular peaks in two-dimensional magnetic resonance spectroscopy and allow for quantification of chemical concentrations in test samples, such as human brain tissue, having complex magnetic resonance spectra due to the presence of numerous chemicals. These new techniques can be used to provide information about the concentrations of a variety of chemicals, including metabolites, in both biological and non-biological media.

19 Claims, 5 Drawing Sheets

TWO-DIMENSIONAL MR SPECTROSCOPY TECHNIQUES

TECHNICAL FIELD

This invention relates to magnetic resonance (MR) techniques, and more particularly to two-dimensional (2-D) magnetic resonance spectroscopy (MRS) techniques.

BACKGROUND

Quantification of chemical concentration using one-dimensional (1-D) MR spectra involves integrating the entire spectrum of a chemical, including all its peaks, along the chemical shift axis to determine the area under the curve. This technique can generally be employed when interference with the spectrum of the chemical of interest by other chemicals is tolerably low. In many samples, including complex biological samples (e.g., the human brain), many chemicals contribute to the 1-D spectrum of the sample, making it difficult to identify and quantify a spectrum for a single chemical of interest. One dimensional MRS techniques have been developed to reduce this interference, such as the multiple quantum filtering spectral editing method, see, e.g., Warren et al., *Journal of Chemical Physics*, 73(5):2512, 1980. These 1-D techniques acquire averaged signals with a constant echo time ($t_e$) and, therefore, the frequency dependence, or J dependence, of the MR signals is not utilized. Consequently, a peak that has a chemical shift coordinate close to a peak of the chemical of interest will overlap and thereby interfere with the nearby peak. In multiple quantum filtering spectral editing, a small residual of the interfering peak can materially alter the peak value of the edited peak of the chemical of interest. Addressing this issue generally involves precise calibration of editing pulse parameters.

Two-dimensional MRS resolves resonance peaks along an additional axis, a frequency axis (J axis), providing more information to differentiate chemical peaks. A 2-D MR spectrum maps frequency in the vertical dimension (D2) against chemical shift, which is the horizontal axis (D1). Thus, in 2-D MRS, peaks having similar chemical shifts can be distinguished in the frequency dimension. Using 2-D MRS (e.g., localized J-resolved 2-D MRS) to analyze samples containing multiple chemicals, peaks that could not be differentiated using 1-D MRS can be resolved, see, e.g., Ke et al., *Psychiatry Research Neuroimaging*, 100: 169, 2000; Ryner et al., *Magnetic Resonance Imaging*, 13(6):853, 1995; Weber, *Technology and Health Care* 5:471, 1997, which are incorporated by reference.

MR signals from J-coupled protons are J modulated, or dependent on $\sin(\pi J t_e)$ or $\cos(\pi J t_e)$, where $t_e$ is the echo time. Each echo corresponds to a free induction decay (FID) signal, which is recorded as data. In J-resolved 2-D MRS experiments, MR signals are acquired using enough different $t_e$ values such that J modulations in signals can be assessed by performing a Fourier transform with respect to $t_e$, see, e.g., W. P. Aue et al., *Journal of Chemical Physics*, 64:4226, 1976; R. R. Ernst et al., *Principles of Nuclear Magnetic Resonance in One and Two Dimensions*, 1988, which are incorporated by reference. According to the relationship between the time and frequency domains in Fourier transform theory, the increments in $t_e$, $\Delta t_e$, determine the bandwidth of the J-frequency dimension. The bandwidth is equal to the inverse of the increments in $t_e$, $1/\Delta t_e$. In 2-D MRS, $\Delta t_e$ is selected to provide a bandwidth that covers the maximum J value of interest and can be adjusted to maximize frequency resolution and signal intensity. For most biological metabolites, J values range from 0 to 20 Hz. Therefore, to use 2-D MRS to assess metabolite concentrations in a region of the human brain, a suitable $\Delta t_e$ can be, e.g., 10 milliseconds (corresponding a bandwidth of 100 Hz) and can be adjusted to produce different bandwidths.

SUMMARY

The present invention concerns identifying appropriate peaks in 2-D MR spectra for 1-D extraction and comparing spectra for test samples to those obtained with reference samples to obtain quantitative measurements of chemical concentrations. These methods can be used to obtain information about, e.g., in vivo chemical concentrations in the human brain using 2-D MRS and offer advantages over 1-D MRS techniques. Test samples can be biological samples, e.g., human or animal tissue, or non-biological samples.

Identifying a suitable peak in a 2-D spectrum for analysis by 1-D extraction involves subjecting a reference sample to a MRS sequence, obtaining a 2-D MR spectrum of the reference sample, and selecting a peak for a chemical of interest in the 2-D MR spectrum by comparing the peaks in the 2-D MR spectrum. It is generally useful to identify peaks that are substantially distinct from other peaks in the 2-D spectrum to reduce interference from other resonance peaks. The peak that is identified can be the peak that is most distinct from any other peaks in the 2-D MR spectrum of the reference sample or the strongest peak that is substantially distinct from the other peaks in the 2-D MR spectrum. With a peak identified, a test sample comprising the chemical of interest is subjected to a MRS sequence, a 2-D MR spectrum of the test sample is obtained, and a 1-D spectrum, i.e., 1-D slice taken along the chemical shift axis, comprising the identified peak for the chemical of interest is extracted from the 2-D MR spectrum of the test sample.

This peak identification methodology can be applied to samples that contain multiple chemicals. If the identified peak for the chemical of interest overlaps with a peak associated with other chemicals in the 2-D MRS spectrum of the test sample, then the 2-D MRS for the reference sample comprising the chemical of interest can be reviewed again to identify the "next best" peak, i.e., another peak substantially distinct from other peaks in the reference sample. In addition, 1-D MR spectra can be extracted from the 2-D MR spectra of multiple test samples. These techniques can be used to observe chemical peaks in 2-D MR spectra that do not suffer from substantial interference with either other peaks from the same chemical or peaks from other chemicals in the test sample. The chemical of interest in these samples can be a metabolite, e.g. gamma-aminobutyric acid (GABA), creatine (Cre), N-acetyl aspartate (NAA), choline (Cho), glutamine, glutamate, alanine, taurine, myo-insitol, glucose, aspartate, or lactate. The identified peak for GABA can be at a chemical shift of about 2.94 ppm, and the identified peak for Cre can be at a chemical shift of about 3.08 ppm.

The invention also generally features methods for quantitative assessment of chemical concentrations. To obtain concentration data, two reference samples containing first and second chemicals, respectively, and a reference chemical (e.g., 3-(trimethylsilyl)-1-propane-sulfonic acid) are subjected to a MRS sequence to obtain 2-D MR spectra. One-dimensional MR spectra, each containing a peak for the first or second chemical, are extracted from these 2-D MR spectra. The selected peaks can be substantially distinct from any other peaks in the 2-D spectra.

Standardized measures of intensity are calculated for each reference sample using the extracted 1-D spectra. This measure of intensity (k) is a ratio of the area under the peak of the first or second chemical (A) in the extracted 1-D MR spectrum of the reference sample to the area under a peak of the reference chemical ($A_{ref}$), multiplied by the concentration of the reference chemical ($\rho_{ref}$), and divided by the concentration of the first or second chemical ($\rho$):

$$k = (A \, \rho_{ref})/(A_{ref} \rho).$$

Using the measures of intensity for the first and second chemicals, a comparison ratio ($R_{21}$) equal to the ratio of the standardized measure of intensity for the second chemical ($k_2$) to the standardized measure of intensity for the first chemical ($k_1$) is calculated:

$$R_{21} = k_2/k_1.$$

This comparison ratio can provide information about the relative concentrations of the first and second chemicals in a test sample. One-dimensional extractions from 2-D MR spectra of a test sample are obtained by subjecting a test sample including the first and the second chemicals of interest to the MRS sequence, obtaining a 2-D MR spectrum of the test sample, and extracting 1-D MR spectra that respectively contain the identified peaks for the first and second chemicals. A test sample ratio ($T_{21}$) is calculated by taking the ratio of the area under the peak of the second chemical in the extracted 1-D spectrum for the second chemical ($A_{test2}$) to the area under the peak of the first chemical ($A_{test1}$) in its extracted 1-D spectrum:

$$T_{21} = A_{test2}/A_{test1}.$$

Dividing the test sample ratio ($T_{21}$) by the comparison ratio ($R_{21}$) yields a relative measure of the concentration of the second chemical ($C_2$) with respect to the first chemical ($C_1$) in the test sample:

$$C_2/C_1 = T_{21}/R_{21}.$$

These quantification techniques can utilize the same parameters as the peak selection techniques and can also be performed repeatedly to obtain measures of relative concentrations for multiple chemicals. Different peaks from the 1-D extractions of the 2-D MR spectra of the reference samples can also be iteratively selected in an attempt to reduce overlap in the 1-D extractions. The calculations can be simplified by using the same concentrations of the reference chemical and/or first and second chemicals in the two reference samples (i.e., where $\rho_{ref1} = \rho_{ref2}$ and/or $\rho_1 = \rho_2$). A Marquadt non-linear curve fitting algorithm is useful for calculating the areas under the peaks. These methods can also provide absolute measures of concentration if a specific concentration of a chemical in the test sample is known or can be estimated.

The 2-D MRS sequence used in these methods can be a J-resolved magnetic resonance spectroscopy sequence and can include a hard 180 radio frequency pulse between two data acquisition periods to reduce total scanning time. Another approach to reduce scanning time is to include interpolation for exponential decay to generate a greater number of data points than the number of data points acquired during MR scanning. Each of these approaches to reducing total scanning time can independently halve the time required.

These new methods offer several advantages compared to quantification techniques using 1-D MR spectra. Reductions in sensitivity to editing pulse parameters and contamination due to T2 decay can be achieved using 2-D MRS techniques. With 2-D MRS, all the available signal can be detected and used as input in the quantitative methodology. In addition, many chemicals can be quantified using 2-D spectra, including most protonated metabolites with J-coupling, e.g., GABA, glutamine, lactate, and alanine. 2-D MRS techniques also enable analysis of a wide range of samples, such as human and animal tissue. These techniques are especially well-suited to study most regions in the human brain.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Magnetic Resonance Techniques

Figure 1:
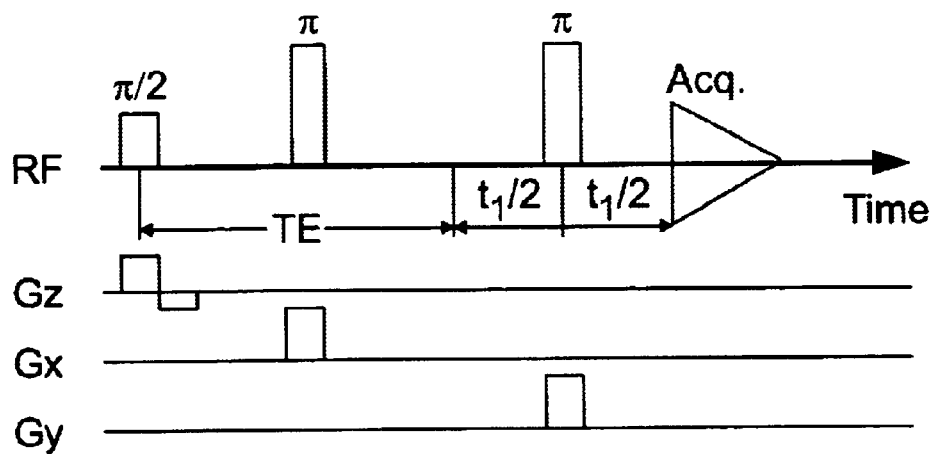
FIG. 1 is a diagram of a magnetic resonance spectroscopy sequence that can be used to acquire two-dimensional magnetic resonance spectra.

FIG. 1 shows an example of a volume localized, J-resolved 2D MRS sequence which is a type of volume selective point resolved echo spectroscopy (PRESS) sequence. In the figure, the RF line shows the RF pulses used in the sequence, while the Gz, Gx, and Gy lines respectively diagram the gradient pulses in the z, x, and y directions. The $\pi$ and $\pi/2$ bars on the RF line denote 180° and 90° pulses, respectively. TE is the time in each sequence before $t_1$, and a data acquisition, Acq., occurs after each $t_1$. In this sequence, there are two waiting periods, $t_{1/2}$, one before and one after the second $\pi$ pulse. The duration of $t_1$ is equal to $t_{10} + N\Delta t_e$, where $N=0, 1, 2 \ldots, N_{max}$, where $t_{10}$ is the minimum $t_1$ and $N_{max}+1$ is equal to the to the number of data points obtained for the D2 dimension. The number of data acquisitions is limited by T2 decay, and a suitable value for $N_{max}$ is, e.g., 63. These sequences are repeated with a chosen repetition time (TR).

Decreasing the time required to obtain spectra is desirable for the comfort of live subjects and to minimize error due to their movement. The sequence shown in FIG. 1 can be modified by including a hard 180° pulse after data has been acquired during the shown data acquisition period. Data can then be collected again during a second data acquisition period after this pulse. Using this approach, scanning time can be halved, since an equal number of data points can be collected before and after this pulse for each sequence. Scanning time can also be reduced by acquiring fewer data points, e.g., half the desired number of data points, and zero-filling to generate a greater number of data points for constructing the two-dimensional magnetic resonance spectrum. Combining these techniques yields even greater reduction in the time required to obtain the MR spectra.

For quantitative measurement, the same sequence and acquisition control parameters are preferably used to obtain MR spectra of both the reference and test samples. The reference sample is generally sampled before the test sample, although this order can be reversed. Also, it is generally desirable to position the test sample in the same space occupied by the reference sample. Peak intensity in the 2-D spectra is a function of the sequence applied to the samples, and consistency permits appropriate scaling from the peak response in the 1-D extractions for the reference sample to calculate chemical concentrations based on peak intensity in the spectra of the test samples.

Figure 2:
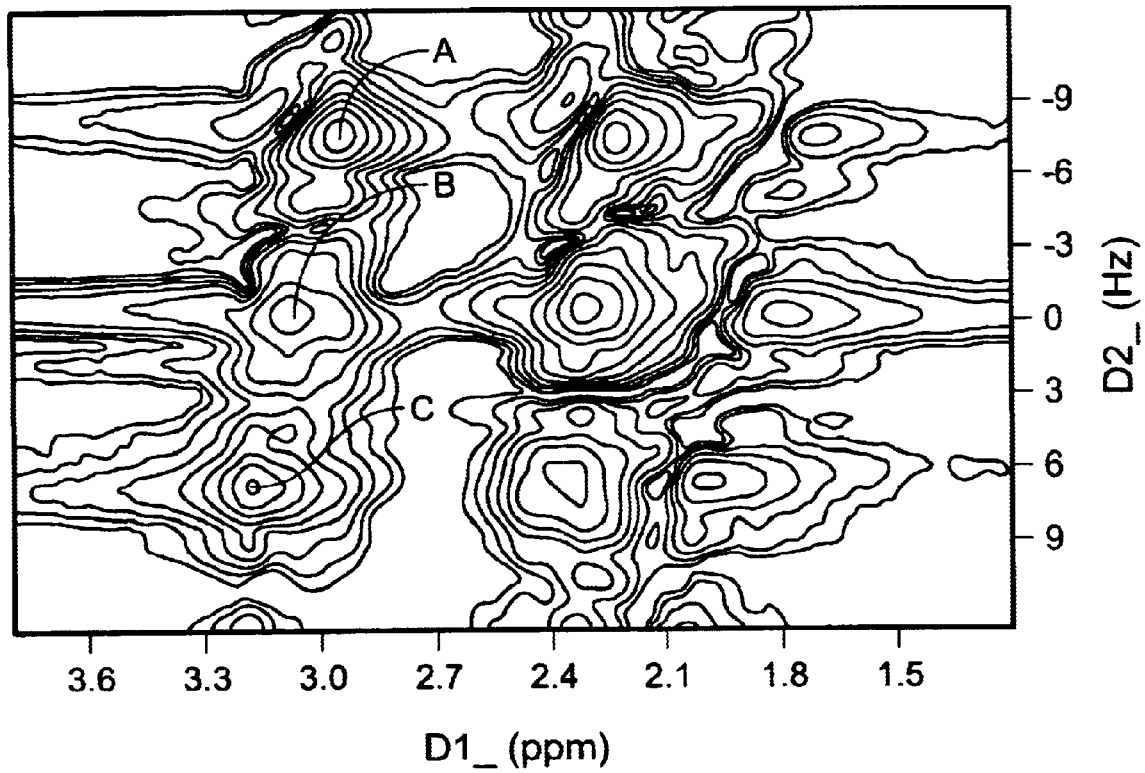
FIG. 2 is a contour plot two-dimensional magnetic resonance spectrum of gamma-aminobutyric acid.

To identify an appropriate peak for 1-D extraction, a reference sample containing a first chemical of interest is subjected to a MRS sequence (e.g., a J-resolved 2-D MRS sequence) to obtain a 2-D MR spectrum. The 2-D MR spectrum of the reference sample includes the peaks of the chemical of interest and also displays peaks for any additional chemicals in the reference sample. Where the chemical of interest is dissolved in a solution of TSPS (3-(trimethylsilyl)-1-propane-sulfonic acid), the main resonance peak of TSPS can be set as the 0 ppm mark in chemical-shift dimension. By setting the peak location of TSPS at 0 ppm on the horizontal axis and the location of a central horizontal line as the 0 Hz mark of vertical axis, all resonance peaks in each 2-D spectrum can then be identified in terms of their 2-D coordinates. FIG. 2 shows a 2-D MR spectrum for a 100 mM GABA ($H_2N-C^4H_2-C^3H_2-C^2H_2-C^1O-HO$) reference sample. FIG. 2 indicates that the two-dimensional resonance peaks for GABA range from 1.78 ppm to 3.20 ppm on the chemical shift axis. These peaks can be separated three groups according to contributions from its C3 (1.7–2.0 ppm), C2 (2.2–2.4 ppm), and C4 (2.9–3.2 ppm) protons. Points A, B, and C in FIG. 2 indicate the three major peaks of GABA from C4 protons.

Figure 3:
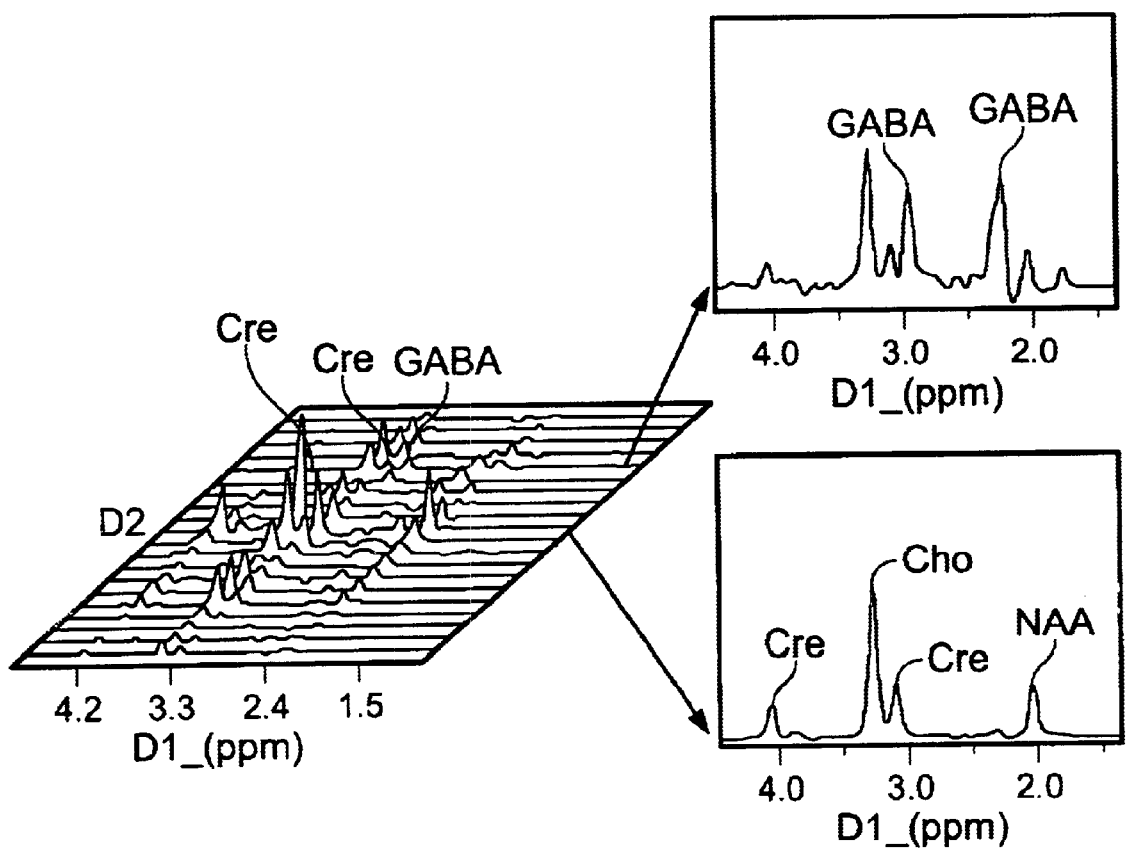
FIG. 3 is a stack plot two-dimensional magnetic resonance spectrum of 100 mM gamma-aminobutyric acid, 100 mM glutamate, 50 mM N-acetyl asparate, 50 mM creatine, and 50 mM choline, with extracted one-dimensional spectra at J=7.45 Hz (upper spectrum) and J=0.0 Hz (lower spectrum).
Figure 4:
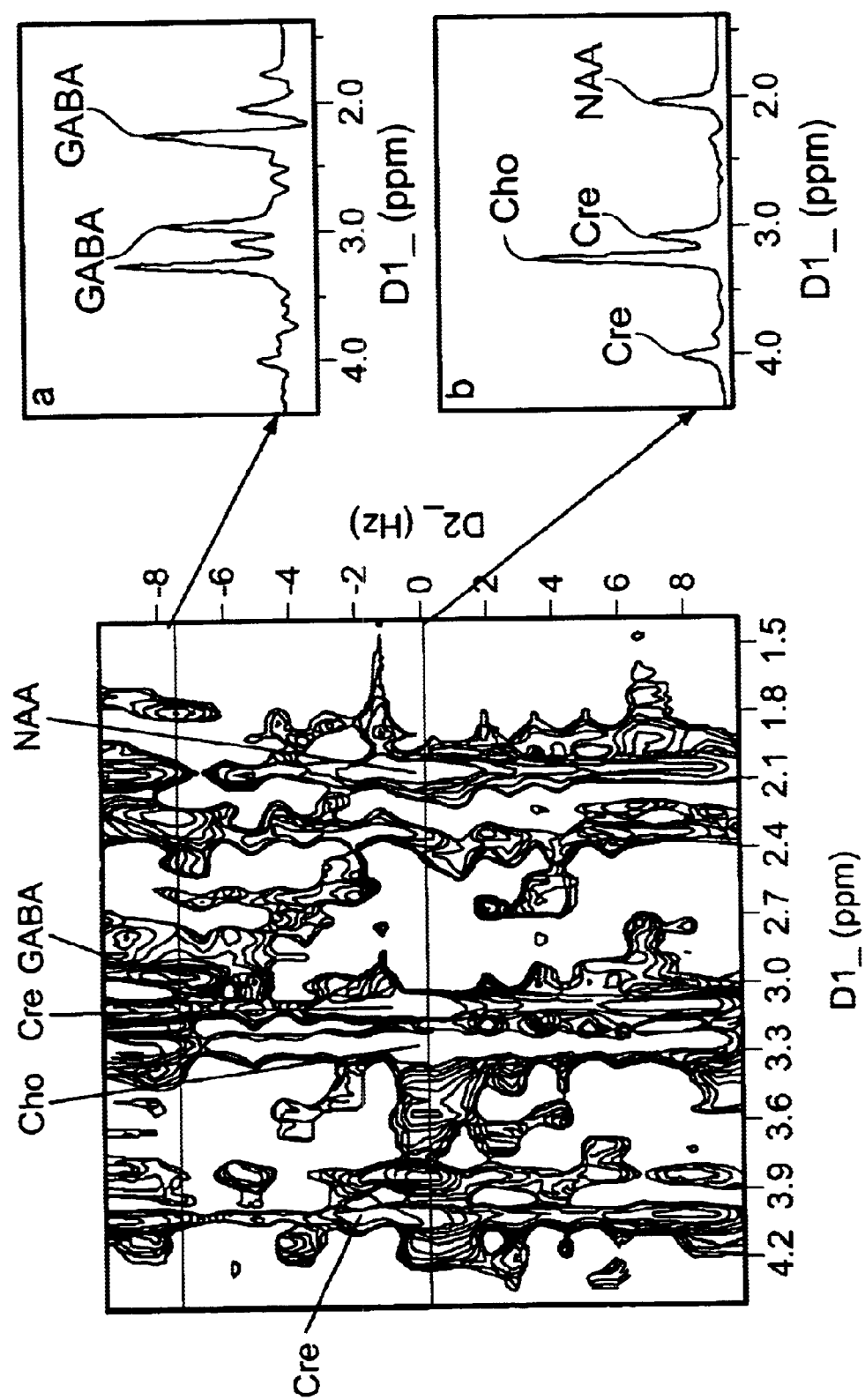
FIG. 4 is a contour plot two-dimensional magnetic resonance spectrum of 100 mM gamma-aminobutyric acid, 100 mM glutamate, 50 mM N-acetyl asparate, 50 mM creatine, and 50 mM choline, with extracted one-dimensional spectra at (a) J=7.45 Hz and (b) J=0.0 Hz.

As long as the user has enough information about the spectra of these chemicals to distinguish the peaks of the chemical of interest from peaks of any additional chemicals, at least for those peaks of the chemical of interest that do not suffer from substantial inference with peaks of additional chemicals, the presence of additional chemicals in the first reference sample will not hamper the ability to identify a peak for the chemical of interest for 1-D extraction. In addition, the presence of additional chemicals permits selection of a peak that does not suffer from substantial interference with these other chemical peaks. FIGS. 3 and 4 show a two-dimensional magnetic resonance spectrum of 100 mM GABA, 100 mM glutamate, 50 mM NAA, 50 mM Cre, and 50 mM Cho. FIG. 3, a stack plot, better illustrates the intensity changes of the Cre and GABA peaks, which can also be observed in the contour plot in FIG. 4. The GABA resonance peaks in the region from 1.7 to 2.4 ppm overlap with resonance peaks from NAA and glutamate, which have similar spectral patterns in this region. The other GABA peaks, labeled A, B, and C in FIG. 2, overlap the Cre and Cho peaks. Of these three, peak A, which is located at (2.94 ppm, 7.45 Hz), overlaps least with its closest neighbor, the Cre peak at 3.08 ppm. At peak A, the intensity of the Cre peak has decreased 92% and its spectral width has decreased 46% from their respective maxima. One-dimensional extraction (a), taken at J=7.45 Hz, shows peak A at 2.94 ppm and its closest neighbor at 3.08 ppm.

Peaks suitable for 1-D extraction are identified by comparing the peaks in the reference sample. It is generally useful to identify a peak that is substantially distinct from any other peaks in the two-dimensional MR spectrum of the reference sample. This peak is characterized by less interference with the signals of other peaks. For example, using the magnetic resonance spectrum in FIG. 3, suitable peaks for GABA and Cre appear at a chemical shifts of approximately 2.94 ppm and 3.08 ppm, respectively. The upper one-dimensional extraction at J=7.45 Hz in FIG. 3 shows the GABA peak at 2.94 ppm, while the lower one-dimensional extraction (extraction (b) in FIG. 4) at J=0.0 Hz shows the Cre peak at 3.08 ppm. Note that the vertical scales in the two one-dimensional extractions are not equal; they were adjusted to display each spectrum fully in each window.

To minimize overlap with other peaks, it can be useful to select the peak in the 2-D MR spectrum of the reference sample that is most distinct, i.e., exhibits the least overlap, with the other peaks in the spectrum. The strength of the peaks in the 2-D MR spectrum can also be considered, and the strongest peak for the chemical of interest that is substantially distinct from the other peaks in the reference sample can be selected.

With a substantially distinct peak identified using this approach, a 1-D MR spectrum can be extracted from a 2-D magnetic resonance spectrum of a test sample. This test sample can be a wide variety of biological and non-biological materials including, e.g., tissue, either in vivo or ex vivo. The test sample is scanned using the same MRS sequence used with the reference sample. Each 1-D slice is subjected to phase correction, ensuring that the extracted 1-D spectrum (slice) will also be correctly phased. A 1-D MR spectrum containing the identified peak is extracted from the 2-D MR spectrum of the test sample. 2-D MR spectra can be obtained for multiple test samples to extract a 1-D MR spectrum containing the selected peak for each test sample.

Where the test sample contains additional chemicals besides the chemical of interest, peaks from these additional chemicals can overlap with the selected peak in the 2-D MR spectrum. If there is overlap between the identified peak and peaks from additional chemicals, another peak for the chemical of interest in the 2-D MR spectrum of the reference can be identified. The extracted 1-D MR spectrum for this new peak can be examined to determine whether it suffers less overlap, and iterative repetition of this process is useful for identifying better peaks based on the degree of overlap.

Quantitative Techniques

These methods can be used to provide relative or absolute quantitative measurements of chemical concentrations in a test sample. To determine relative chemical concentrations in a test sample, reference samples are prepared, each having a known concentration of a chemical of interest. These reference samples also each contain a known concentration of a reference chemical. The reference chemical is needed to provide a standardized (or reference) measure of intensity for each reference because absolute signal response varies between experiments, even when using the same MRS sequence. Among the reference chemicals commonly used in proton MRS is TSPS, since its peaks are located far away from those of most biological chemicals of interest (e.g., NAA, Cre, Cho, or GABA) and therefore do not present an interference problem. While there is no theoretical limit on the concentrations of the chemical of interest and reference chemical in the references, it is practical to have high enough concentrations to permit easy and accurate generation of 2-D MRS spectra. For example, 30 mM concentrations of metabolites in 3 mM TSPS are suitable. In addition, using the same concentration of metabolites and/or the reference chemical can simplify comparison.

Even where numerous chemicals of interest are being investigated, it is only necessary to consider the relationship between pairs of reference samples, a first reference sample and a second reference sample, to provide a basis for obtaining relative information about concentrations in the test sample. The 2-D MR spectra for these reference samples are collected using the same 2-D MR sequence, e.g., a J-resolved MRS sequence, since using different sequences can affect the MR spectra. Where the chemicals of interest are unstable, it is desirable to obtain their spectra promptly after the reference samples are prepared or to keep the chemicals in an environment (e.g., low temperature) that maintains their stability for as much of the experiment time as possible.

One-dimensional MR spectra comprising peaks for the first and second chemicals are extracted. It is often useful to select the peak that is most distinct from any other peaks in the 2-D spectrum, or the strongest peak that is substantially distinct from the other peaks. Another peak can be identified if the extracted 1-D spectrum for that chemical presents overlap between the peak for that chemical and other peaks from the test sample. This process can be repeated to identify chemical peaks that overlap less with other peaks in the test sample. If the extracted spectrum for each reference does not contain the peak of the reference chemical to be used in calculating the standardized measure of intensity, another 1-D spectrum is extracted that includes that reference peak.

The measure of intensity for each chemical (k) is the ratio of the area under the peak for that chemical in the extracted 1-D spectrum (A) to the area of the peak for the reference chemical ($A_{ref}$), multiplied by the concentration of the reference chemical ($\rho_{ref}$), and divided by the concentration of the chemical of the chemical of interest ($\rho$). A fitting algorithm, e.g., a non-linear curve fitting algorithm such as the Marquadt algorithm, can be used to model the peaks for area calculation. This standardized measure of intensity is useful because it can be compared to samples processed in different experiments; therefore, the first and second reference samples can be scanned separately. Using the standardized measures of intensity for the two chemicals, one can compute a comparison ratio ($R_{21}$) that indicates the peak strength of the second chemical with respect to the first for the same concentration of the first and second chemicals. This comparison ratio ($R_{21}$) is the ratio of the standardized measure of intensity of the second chemical ($k_2$) to the standardized measure of the intensity of the first chemical ($k_1$).

This comparison ratio permits assessment of the relative concentrations of the first and second chemicals in a test sample. Using a 2-D MR spectrum of a test sample, 1-D MR spectra can be extracted for the relevant peaks of the first and second chemicals. The test sample ratio ($T_{21}$) is calculated as the ratio of the area under the peak of the second chemical ($A_{test2}$) to the area under the peak of the first chemical ($A_{test1}$) in the extracted 1-D spectra for the test sample. The relative measure of concentration of the second chemical ($C_2$) to the first chemical ($C_1$) is the test sample ratio divided by the comparison ratio ($R_{21}$). Therefore, if either concentration is known, or can be estimated or assumed, the concentration of the other chemical can be derived using the relative measure of concentration by straightforward multiplication. These procedures permit analysis of the concentrations of numerous chemicals by repeatedly performing pair wise comparison. This quantitative data has numerous application including, e.g., assessment of chemical response to stimuli and diagnosis of medication conditions based on measurements of in vivo levels of chemicals in localized regions of humans or animals.

EXAMPLES

The invention is further described in the following examples, which do not limit the scope of the invention described in the claims.

Example 1

Assessment of Absolute in vivo GABA Concentration in the Human Brain

The new methods have been used to quantify in vivo GABA levels in the human brain. A 1.5 Tesla MR scanner was used to acquire volume localized, J-resolved 2-D MRS data from reference samples and the occipital lobe of healthy volunteers. Use of a 2.1 Tesla MR scanner could yield approximately 40% higher signal intensities. The MRS sequence used in these experiments was a variant of the volume selective PRESS sequence shown in FIG. 1. In these experiments, the minimum $t_e$ ranged from 48 to 678 milliseconds, $\Delta t_e$ was 10 milliseconds (corresponding to a frequency bandwidth of 100 Hz), and TR was 2.64 milliseconds. A free induction decay (FID) signal was recorded for each specific $t_e$, creating a total data set of 1024 data points for the D1 dimension and 64 data points for the D2 dimension of the 2-D MR spectrum. A vertical resolution of 0.78 Hz was achieved by zero-filling before taking the Fourier transform.

Phantoms containing 350 milliliters of solution were prepared in round Erlenmeyer flasks and data were obtained from a cubic voxel of 27 $cm^3$ in the center of the phantom. The phantoms contained (1) 100 mM GABA and mixtures of 100MM GABA with: (2) 100 mM glutamate and 50 mM NAA, Cre, Cho, (3) 100 mM glutamate, and (4) 100 mM glutamine. As shown in FIGS. 3 and 4, the GABA peak located at (2.94 ppm, 7.45 Hz) and the Cre peak located at (3.08 ppm, 0 Hz) were selected for use in quantitative measurement. While this selection was not automated in these experiments, peaks can be selected using a processor that performs a peak-selection algorithm. The algorithm can, e.g., take peak location and mean width at half height into account in determining the degree of overlap among peaks and can select a peak to minimize overlap or based on a formula that weights factors for overlap and peak strength. In addition, this algorithm can operate iteratively in an attempt to identify better peaks on successive iterations.

Figure 5:
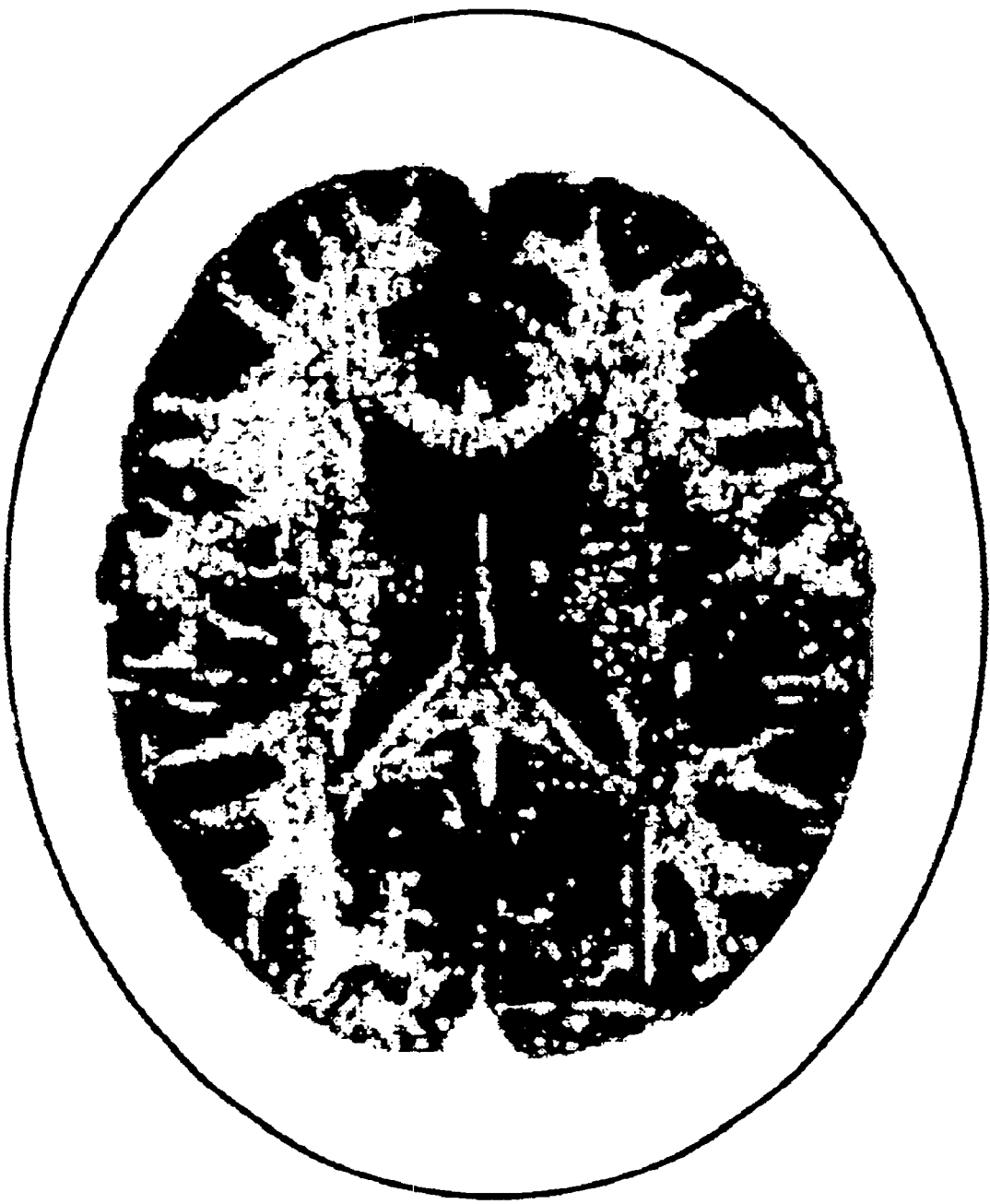
FIG. 5 is a MR image of the human brain, with a black box to indicate a voxel in the left occipital lobe.

Using the localized J-resolved 2D MRS sequence shown in FIG. 1, 36 J-resolved 2-D MR spectra were collected from 18 male and 18 female subjects using a GE 1. 5T MR scanner and a standard quadrature head coil. The head coil can be replaced with a surface coil, which increases receiver sensitivity by a factor of two, see, e.g., Wald et al., *Magnetic Resonance in Medicine,* 34(3):440, 1995, which is incorporated by reference. After sagittal and axial MRI scans for spectroscopy localization, a 2×3×2 cm³ voxel was positioned mainly within the gray matter of the left occipital lobe in each subject. The location of this voxel in the brain is shown in FIG. 5. Total scanning time, including the MRI scans for spectroscopy localization, was 40 min. For water suppression, three chemical shift selective (CHESS) pulses were applied prior to the localized J-resolved 2D MRS sequence, see, e.g., Haase et al., *Physics in Medicine and Biology,* 30(4):34, 1985; Matthaei et al., *Radiology,* 160(3):791, 1986; Frahm et al., *Magnetic Resonance in Medicine,* 9(1):79, 1989, which are incorporated by reference.

Figure 6:
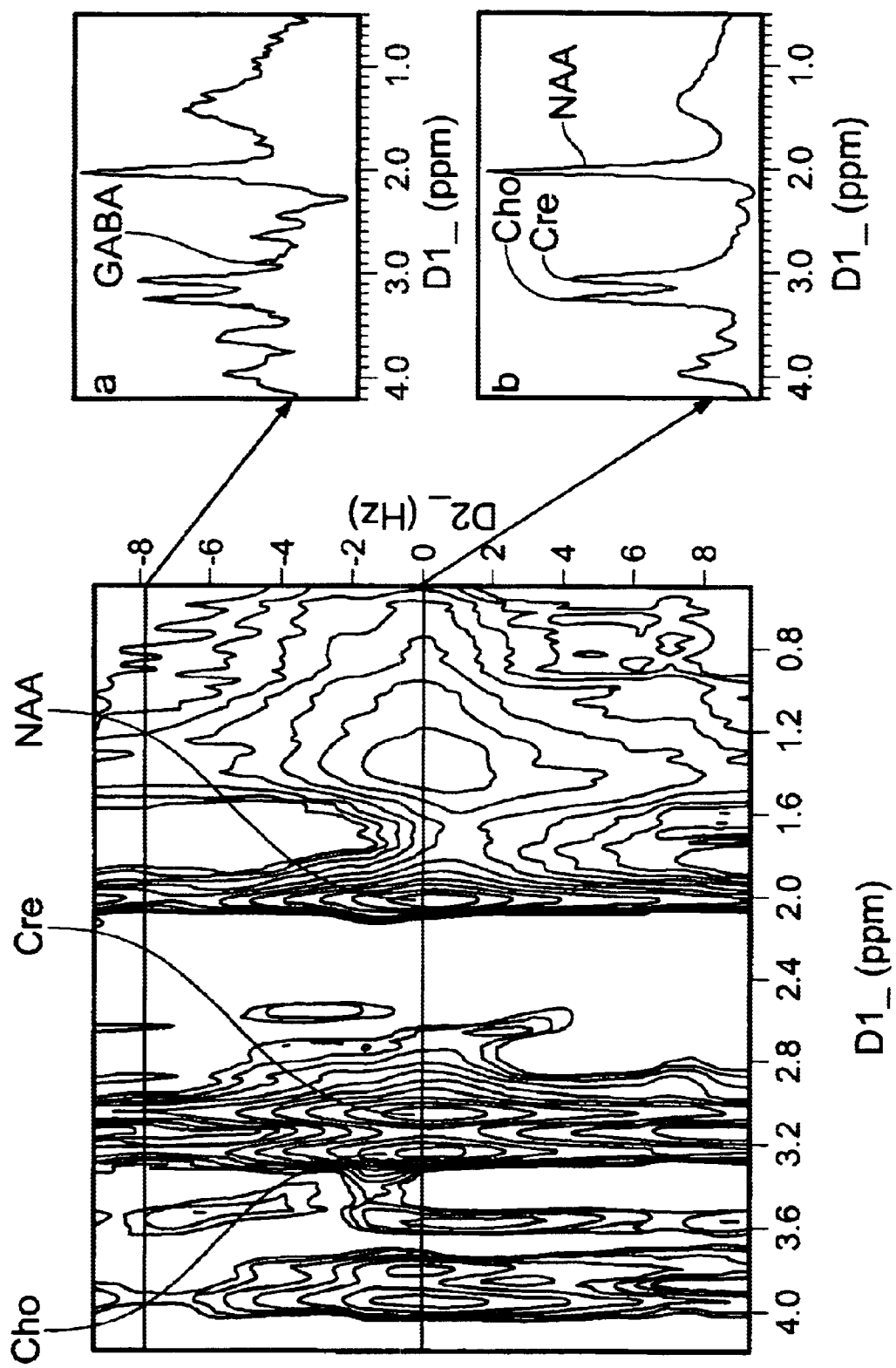
FIG. 6 is a two-dimensional magnetic resonance spectrum of a voxel in the left occipital lobe of the human brain with extracted one-dimensional spectra at (a) J=7.45 Hz and (b) J=0.0 Hz.

Data processing was performed using a SUN® Ultra™ 5 workstation. Commercial software for 2D MRS processing, FELIX nD (MSI, San Diego, Calif.), was modified to produce a fully automated processing algorithm. Prior to 2-D Fourier transformation, time domain data points were doubled by zero filling and a 2 Hz exponential function was applied in both the D1 and D2 dimensions. After 2-D Fourier transformation, all 1-D chemical-shift spectra were automatically phased individually using a zero order phase correction, which allowed use of the real part of complex spectrum for spectral line fitting. FIG. 6 shows the 2-D MR spectrum of the chosen voxel in the left occipital lobe, with 1-D extractions at (a) J=0 Hz and (b) J=7.45 Hz. The GABA and Cre resonance peak areas were obtained from the extracted 1-D spectra (a) and (b) in FIG. 6 by using conventional Marquadt 1-D spectral fitting methods. In this 1-D spectral fitting, the real part of the GABA and Cre peaks were fitted as Lorentzian peaks.

Using reference samples, the measure of intensity for Cre was found to be twelve times higher than that for GABA, yielding a comparison ratio for GABA to Cre of 1 to 12.

The mean creatine concentration was assumed to be 8 $\mu$mol/cm³, see, e.g., Lowry et al., *Journal of Neurochemistry,* 29(6):959, 1977; Petroff et al., *Neurology,* 39(9):1197, 1989; Rothman et al., *Proceedings of the National Academy of Sciences USA,* 90(12):5662, 1993, which are incorporated by reference. Dividing the ratio of the peak area of GABA to Cre in the chosen voxel by the comparison ratio, multiplying by the assumed 8 $\mu$mol/cm³ concentration of Cre, and averaging over subjects of the same sex, the mean concentration of GABA in the male patients was 1.01±0.36 $\mu$mol/cm³ and 1.16±0.43 $\mu$mol/cm³ in female subjects. Thus, the women had 15.5% higher mean brain GABA concentrations than the men. Although this difference was not statistically significant for the number of subjects studied (p=0.12), it is in good agreement with the recent report by Sanacora and colleagues, see, Sanacora et al., *Archives of General Psychiatry,* 56(11):1043, 1999. Gender differences in brain GABA levels may be of great importance in explaining the different population risk and treatment response of men and women with alcoholism, mood, and anxiety disorders.

Example 2

Response of Frontal Lobe Metabolite Levels to Treatment for Cocaine Dependence In this experiment, brain metabolite levels in the prefrontal cortex of cocaine dependent and matched comparison subjects for groups of 28 subjects were assessed and compared. Using J-resolved 2-D MRS in vivo J-resolved 2-D MR spectra were acquired from a voxel of 18.75 cm³ centered on the left dorsolateral prefrontal cortex using the same parameters as in Example 1, except TR was 2.32 seconds. With the use of phased array receivers for the frontal voxel, receiver sensitivity was increased by over four fold compared to the GE quadrature head coil. This permitted a four-fold reduction in the number of averages collected, while maintaining a comparable signal to noise ratio. Total scanning time for each 2-D MR spectrum was less than 20 minutes.

All 2-D spectra were processed using modified Felix nD (MSI, San Diego) software, and spectral results for GABA and other resonance peaks were converted to chemical concentrations in units of $\mu$M/cm3. Using the new methods to obtain standardized measures of intensity for the metabolities of interest, the comparison factors used for this study were: GABA: Cho: Cre: NAA=0.083: 3.5 :1: 1.25. These comparison factors were obtained from phantom studies of these chemicals using identical acquisition parameters. All data analyses were performed using Statview (Version 5.0, 1998). Between group differences in terms of demographic characteristics were determined using either analysis of variance (ANOVA) or contingency table analyses. For comparison of neurochemical measures, single or repeated measures ANOVA methods were employed. Significance was defined as p<0.05.

At baseline, GABA levels were significantly lower in the cocaine dependent subjects (N=36) than in the comparison subjects (N=15) (F=8.68, p=0.0049). No baseline differences in NAA (F=0.33, p=0.86) or Cho (F=0.003, p=0.96) were noted. For the 28 subjects who completed the clinical trial, brain GABA levels were increased by 10.32% (F=4.8, p=0.04). No changes in either NAA (F=0.15, p=0.70) or Cho (F=0.26, p=0.62) were noted over the same interval. Based on self-report data, cocaine-dependent subjects were classified as either responders (subjects with >25% decreased cocaine use) or non-responders (subjects who had <25% decreased cocaine use). Brain GABA levels increased by 14.1% in responders (F=5.8, p=0.03) and 4.9% in non-responders (F=0.49, p=0.49). Increased brain GABA levels were noted in cocaine-dependent subjects treated with venlafaxine (F=12.416, p=0.0078) and pramipexole (F=3.410, p=0.1020), but not with placebo (F=0.124, p=0.7330).

A number of embodiments of the invention have been described. Nevertheless, it will be understood that various modifications may be made without departing from the spirit and scope of the invention. For example, the techniques can be applied to analyze concentrations in other forms of tissue besides brain tissue, e.g., breast tissue, prostrate tissue, and kidney tissue, and can be used in 2-D MR spectroscopy of non-biological samples. Accordingly, other embodiments are within the scope of the following claims.

What is claimed is:

1. A method for obtaining a relative measure of concentrations of metabolites in vivo comprising:
    (a) subjecting a first reference sample comprising a known concentration of a first metabolite and a known concentration of a reference metabolite to a magnetic resonance spectroscopy sequence;
    (b) obtaining a two-dimensional magnetic resonance spectrum of the first reference sample;
    (c) extracting a one-dimensional magnetic resonance slice comprising a peak for the first metabolite and a peak for the reference metabolite, wherein the peak M the first metabolite is identified by comparing peaks in the two-dimensional magnetic resonance spectrum of the first reference sample to select a peak that is substantially distinct from other peaks in the two-dimensional magnetic resonance spectrum;

(d) calculating a correlation factor for the first metabolite, wherein the correlation factor is a ratio of a peak integral for the first metabolite to a peak integral for the reference metabolite, multiplied by a ratio of the concentration of the reference metabolite to the concentration of the first metabolite;

(e) subjecting a second reference sample comprising a known concentration of a second metabolite and a known concentration of the reference metabolite to the magnetic resonance spectroscopy sequence;

(f) obtaining a two-dimensional magnetic resonance spectrum of the second reference sample;

(g) extracting a one-dimensional magnetic resonance slice comprising a peak for the second metabolite and a peak for the reference metabolite, wherein the peak for the second metabolite is identified by comparing peaks in the two-dimensional magnetic resonance spectrum of the second reference sample to select a peak that is substantially distinct from other peaks in the two-dimensional magnetic resonance spectrum;

(h) calculating a correlation factor for the second metabolite, wherein the correlation factor is a ratio of a peak integral for the second metabolite to a peak integral the reference metabolite multiplied by a ratio of the concentration of the reference metabolite to the concentration of the second metabolite;

(i) calculating a comparison ratio, wherein the comparison ratio is the ratio of the correlation factor for the second metabolite in the second reference sample to the correlation factor for the first metabolite in the first reference sample;

(j) subjecting a test sample comprising the first metabolite and the second metabolite to the magnetic resonance spectroscopy sequence;

(k) obtaining a two-dimensional magnetic resonance spectrum of the test sample;

(l) extracting a one-dimensional magnetic resonance slice front the two-dimensional magnetic resonance spectrum of the test sample comprising the peak for the first metabolite;

(m) extracting a one-dimensional magnetic resonance slice from the two-dimensional magnetic resonance spectrum of the test sample comprising the peak for the second metabolite;

(n) calculating a test sample ratio, wherein the test sample ratio is the ratio of a peak integral or the second metabolite in the extracted one-dimensional slice for the second metabolite in the test sample to a peak integral of the first metabolite in the extracted one-dimensional slice for the first metabolite in the test sample; and (o) obtaining a relative measure of the concentration of the second metabolite in the test sample compared to the concentration of the first metabolite in the test sample by dividing the test sample ratio by the comparison ratio.

2. The method of claim 1, wherein the peaks identified for the first and second metabolites are peaks that are substantially distinct from any other peeks in the two-dimensional magnetic resonance spectrum of the first and second reference samples.

3. The method of claim 1, wherein the reference chemical is 3-trimethylsilyl-1-propane-sulfonic acid (TSPS).

4. The method of claim 1, wherein the peak for the first metabolite is the peak that is most distinct from any other peak in the two-dimensional magnetic resonance spectrum of the first reference sample and the peak for the second metabolite is the peak that is most distinct from any other peak in the two-dimensional magnetic resonance spectrum of the second reference sample.

5. The method of claim 1, further comprising selecting a strongest peak for the first metabolite from those peaks for the first metabolite that are substantially distinct from any other peaks in the two-dimensional magnetic resonance spectrum of the first reference sample and selecting a strongest peak for the second metabolite from those peaks for the second metabolite that are substantially distinct from any other peaks in the two-dimensional magnetic resonance spectrum of the second reference sample.

6. The method of claim 1, wherein the test sample is tissue.

7. The method of claim 6, wherein the test sample is human brain tissue.

8. The method of claim 1, wherein the first and second metabolites are gamma-aminobutyric acid, creatine, N-acetyl aspartate, choline, glutamine, glutamate, alanine, taurine, myo-insitol, glucose, aspartate, or lactate.

9. The method of claim 8, wherein the peak for gamma-aminobutyric acid is at a chemical shift of about 2.94 ppm.

10. The method of claim 8, wherein the selected peak for creatine is at a chemical shift of about 3.08 ppm.

11. The method of claim 1, wherein the magnetic resonance spectroscopy sequence is a J-resolved magnetic resonance spectroscopy sequence.

12. The method of claim 1, wherein the two-dimensional magnetic resonance spectrum is constructed using zero-filling.

13. The method of claim 12, wherein the zero-filling generates twice the number of data paints acquired in the magnetic resonance sequence.

14. The method of claim 1, further comprising repeating steps e) through o) to obtain measures of relative concentrations for multiple metabolites.

15. The method of claim 1, wherein the concentration of the reference metabolite is the same in the first reference sample and the second reference sample.

16. The method of claim 1 or claim 14, wherein the concentrations of the first end second metabolites are equal.

17. The method of claim 1, further comprising multiplying a specific concentration of the first metabolite in the test sample by the relative measure of concentration to calculate a specific concentration of the second metabolite in the test sample.

18. The method of claim 1, wherein the peak integrals are computed using a Marquadt non-linear curve fitting algorithm.

19. The method of claim 1 further comprising:

(p) examining the extracted one-dimensional magnetic resonance slices of the peaks for the first and second metabolites from the test sample for overlap with any other peak;

(q) if there is overlap between the peak for the first metabolite or the peak for the second metabolite and any other peak, identifying a new peak for that metabolite in the two-dimensional magnetic resonance spectrum of the reference sample for that metabolite that is substantially distinct from any other peaks in the two-dimensional magnetic resonance spectrum of the reference sample; and (r) repeating steps p) and q) to identify a peak for that metabolite having less overlap with any other peak in the extracted one-dimensional slice of the test sample for that chemical.

* * * * *